United States Patent
Garfield et al.

(10) Patent No.: US 6,613,757 B1
(45) Date of Patent: Sep. 2, 2003

(54) COMBINATION OF PROSTACYCLIN WITH AN ESTROGEN OR PROGESTIN FOR THE PREVENTION AND TREATMENT OF ATHEROSCLEROTIC VASCULAR DISEASE INCLUDING PREECLAMPSIA AND FOR THE TREATMENT OF HYPERTENSION, AND FOR HORMONE REPLACEMENT THERAPY

(75) Inventors: Robert E. Garfield, Friendswood, TX (US); Kristof Chwalisz, Berlin (DE)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 08/310,950

(22) Filed: Sep. 22, 1994

(51) Int. Cl.⁷ .................. A61K 31/58; A61K 31/56; A61K 31/66
(52) U.S. Cl. ................ 514/176; 514/75; 514/179
(58) Field of Search ................ 514/176, 179, 514/75

(56) References Cited

U.S. PATENT DOCUMENTS 4,879,285 A * 11/1989 O'Neill ................ 514/75

OTHER PUBLICATIONS

Michael R. Adams, et al., "*Effects of Estrogens and Progestins on Atherosclerosis in Primates*", pp. 161–173 (1992).

Meir J. Stampfer, "*A Review of the Epidemiology of Postmenopausal Estrogens and the Risk of Coronary Heart Disease*", pp. 177–195. (1992).

W. Skuballa, et al., "*Chemistry of Stable Prostacyclin Analogues: Synthesis of Iloprost*", Department of Chemistry, Research Laboratories of Schering AG, Berlin, Germany (1985).

M. Braun, et al., *Antiatherosclerotic Properties of Oral Cicaprost in Hypercholesterolemia Rabbits*, Institut für Pharmakologie and Institut für Pathologie, Heinrich–Heine–Universität Düsseldorf, Moorenstr. 5, D–4000 Düsseldorf 1, Germany (1992).

Th. Hohfeld, et al., "*Oral Cicaprost Reduces Platelet and Neutrophil Activation in Experimental Hypercholesterolemia*", Institut für Pharmakologie, Heinrich–Heine–Universität Düsseldorf, Moorenstr. 5, D–4000 Düsseldorf, Germany (1992).

I. Woditsch, et al., "*Oral Cicaprost Protects from Hypercholesterolemia–Induced Impairment of Coronary Vasodilation*", Institut für Pharmakologie, Heinrich–Heine–Universität Düsseldorf, Moorenstr. 5, D–4000 Düsseldorf, Germany (1992).

G.A. Burton, et al., "*Iloprost Preserves Endolethelial Function Against Cyclosporin A and Sensitises Microvessels Towards Endothelium–Dependent and –Independent Vasodilatation*", Research Laboratories of Schering AG, Department of Cardiovascular Pharmacology, Müllerstr. 170–178, W–1000 Berlin 65, Germany (1992).

* cited by examiner

Primary Examiner—Theodore J. Criares

(57) ABSTRACT

Cardiovascular disease, including preeclampsia in pregnant women and hypertension in both women and men, are prevented or treated by administering thereto prostacyclin or a prostacyclin analog in combination with one or both of an estrogen and a progestin, which combination is also useful for HRT in peri- and post-menopausal women.

23 Claims, 6 Drawing Sheets

COMBINATION OF PROSTACYCLIN WITH AN ESTROGEN OR PROGESTIN FOR THE PREVENTION AND TREATMENT OF ATHEROSCLEROTIC VASCULAR DISEASE INCLUDING PREECLAMPSIA AND FOR THE TREATMENT OF HYPERTENSION, AND FOR HORMONE REPLACEMENT THERAPY

BACKGROUND OF THE INVENTION

This invention relates to a method for the prevention and treatment of atherosclerotic vascular disease (cardiovascular disease); for the prevention and treatment preeclampsia in pregnant women and for hormone replacement therapy in peri- and post-menopausal women, and for the treatment of hypertension in women and men.

Epidemiological data indicate that approximately one half of the deaths in economically developed countries are attributable to a single major cause, viz., cardiovascular disease, including coronary heart disease, stroke and other forms of vascular disease (Green, A., Bain, C., 1993). The commonest and most lethal form of cardiovascular disease is coronary heart disease. In men, there is a continuous increase in the prevalence of cardiovascular disease after the age of 30–40 years. On the other hand, the rate of cardiovascular disease, especially coronary heart disease, is relatively low among premenopausal women but rises sharply with increasing age, suggesting that sex steroids (estrogens and progesterone) have a protective effect in women. The increased risk of coronary heart disease among women with bilateral oophorectomy further supports the view that steroid hormones may play a protective role with regard to cardiovascular disease.

Cardiovascular disease can be prevented in postmenopausal women by hormone replacement therapy (HRT) with estrogens. The recently performed meta-analysis of 29 studies has demonstrated a reduced cardiovascular disease risk among estrogen users in 23 of these studies (Stampfer et al., 1991). There is also experimental evidence from studies in monkeys that the development of coronary atherosclerosis induced by oophorectomy and diet may be reversed by estrogen supplementation (Adams et al., 1992). On the other hand, there are no effective methods for the prevention of cardiovascular disease in man, since estrogen cannot be used because of side-effects.

The mechanism of the protective effect of female sex hormones is not fully understood. An impact on the lipid profile may be possible. Among postmenopausal women, estrogens reverse the atherogenic changes in lipid profile which is associated with early menopause such as the increase in LDL-cholesterol and serum triglyceride levels and the decrease in HDL-cholesterol. However, new data suggest that both estrogens and progesterone may have a direct effect on the blood vessels. The presence of estrogen and progesterone receptors in arterial endothelial and smooth muscle cells supports the view that sex steroids may have a direct effect on the blood vessels (Lin et al., 1986). It has also been demonstrated that estrogen treatment results in the redistribution of arterial estrogen receptors and in the increase in arterial progesterone receptors in baboons (Lin et al, 1986). Monkey studies suggest that the estrogens may prevent ovariectomy-induced atherosclerosis by inhibiting the uptake and degradation of LDL in the arterial wall (Adams et al., 1992). The effects of estrogens and/or progesterone on arterial tone may also explain some of the beneficial effects of HRT on arterial disease risk. From animal models it is known that estrogens increase uterine blood flow by regulating the vascular tone (Greiss & Anderson, 1970, Ganger et al., 1993). The effects of a sex steroid on the vascular tone suggest that sex steroids may play a role in the pathogenesis of hypertension.

The effects of steroids on the vessels can be mediated by various locally produced hormones including nitric oxide, prostacyclin and endothelin. Both nitric oxide and prostacyclin induce vascular relaxation and inhibit platelet aggregation. On the other hand, endothelin has a strong vasoconstriction effect. Nitric oxide is produced by endothelial cells and is involved in the regulation of vascular tone, platelet aggregation, neurotransmission and immune activation (Furchgott and Zawadzki, 1980; Moncada, Palmer and Higgs, 1991). Nitric oxide, formerly known as EDRF (endothelin-derived relaxing factor) (Furchgott und Zawadzki, 1980; Moncada, Palmer and Higgs, 1991), is synthesized by the oxidative deamination of a guanidino nitrogen of L-arginine by at least three different isoforms of a flavin-containing enzyme, nitric oxide synthase (Moncada, Palmer and Higgs, 1991). Nitric oxide elevates levels of cGMP (1,3,5-cyclic guanosine monophosphate) within the vascular smooth muscle to produce relaxation and to reduce blood vessels tone (Moncada, Palmer and Higgs, 1991).

Prostacyclin is a potent endogenous platelet inhibitory and antithrombogenic substance acting as a local regulator of cell-vessel wall interaction (Willis and Smith 1989). The pharmacological effects of prostacyclin are similar to those of nitric oxide. It is a potent vasodilator which dose-dependently lowers peripheral arterial resistance and blood pressure. The clinical use of prostacyclin is limited due to its chemical instability. Therefore, a prostacyclin analog is preferred, i.e., a prostaglandin derivative with a structure related to prostaglandin which exhibits an effect on the cardiovascular system, e.g., inhibitions of platelet aggregation. Iloprost an cicapristost are stable analogs of prostacyclin. Iloprost was the first compound synthesized that combined the biological profile of prostacyclin with chemical stability (Skuballa et al., 1985). Cicaprost is a metabolically and chemically stable prostacyclin analog which shows high bioavailability and prolonged duration of action (Skuballa et al., 1986). It is highly specific prostacyclin mimic, exhibiting only minor if any effects on organ systems sensitive to other prostaglandins.

There is evidence that prostacyclin analogs exert protective effects on the endothelium. Beneficial effects of cicaprost and iloprost on atherosclerosis were described in animal models. Oral treatment of cholesterol-fed rabbits with cicaprost reduced aortic atheromatous plaque formation and partially prevented hypercholesterolemia-induced impairment of endothelium-dependent relaxation (Braun, M., et al., 1992). In addition, cicaprost reduced hypercholesterolemia-induced platelet and neutrophil hyperactivity in rabbits (Hohfeld et al., 1992). Platelets and leukocytes are believed to contribute to atherogenesis. Furthermore, studies in rabbits showed that oral cicaprost has a beneficial effect on the hypercholesterolemia-induced impairment of coronary vasodilatation (Woditsch I, et al., (1992). Iloprost has been found to protect microvascular arteriolar endothelium from damage by cyclosporin (Burton GA et al., 1992).

These animal studies suggest that prostacyclin analogs alone may be protective against atherosclerosis. There are no experimental or clinical studies with a combination of prostacyclin analogs with a progestin or an estrogen.

Preeclampsia is a pregnancy-specific disease classically defined as the triad of hypertension, pathologic edema and proteinuria normally associated with fetal hypotrophy. The etiology and pathogenesis of this common disease (approximately 10% of all pregnancies) is poorly understood. It is generally believed that preeclampsia is linked to prostacyclin deficiency and increased thromboxane A2 production. The current therapy is restricted to bed rest (mild form), symptomatic medication with antihypertensive drugs and early delivery with attendant risks of operative delivery and iatrogenic prematurity. In preeclampsia, there is a reduced preload, low cardiac output and an elevated afterload which is consistent with a decreased intravascular volume and an increased peripheral vascular resistance. The increased peripheral resistance has been explained by (1) the increased vascular sensitivity to pressor agents and (2) the presence of a vasoactive substance. There is considerable evidence that preeclampsia is associated with an increased sensitivity to the pressor effects of angiotensin 11 and other vasoactive agents (Abdul-Karim 1961, Gant 1973, Gant 1974), platelet activation (Bonnar 1971, Perkins 1979, Giles 1981), and endothelial cell injury (Roberts 1989, Shanklin 1989). The prominent clinical features of preeclampsia, edema and proteinuria are consistent with the loss of endothelial transport function.

Preeclampsia is often considered as an acute form of atherosclerosis. The spiral arteries that perfuse the intervillous space of normal placenta undergo extensive morphological changes during normal pregnancy, viz., a fourfold increase in diameter and a loss of their muscular and elastic components (Robertson 1986). These changes allow for an approximate tenfold increase in uterine blood flow that occurs during normal gestation. These changes are absent in preeclampsia (Robertson 1986) so that the intramyometrial segments of the spiral arteries are unable to dilate. In addition, the basal arteries and myometrial segments of spiral arteries in the preeclamptic placenta demonstrate characteristic lesions which have been called "acute atherosis" (Roberts 1989). In acute atherosis of the preeclampsia uterus there is an endothelial cell injury, a focal interruption of the basement membrane, platelet deposition lipoid necrosis of muscle cells (foam cells), (a result of chronic hypoxia and/or cytotoxins), mural thrombi and fibrinoid necrosis (Robertson 1967, DeWolf 1980, Roberts 1989), effects very similar to those seen in atherosclerotic vascular disease.

There is also evidence that prostacyclin production is decreased in preeclampsia. In a normal pregnancy there is an approximately 5–10-fold increase in prostacyclin production compared to the non-pregnant state (Goodman 1982, Walsh 1985, Fitzgerald 1,987). In contrast, there is a decreased production of prostacyclin in maternal, placental and umbilical cord vessels and in placental cotyledons (Remuzzi 1980, Makila 1984, Walsh 1985) in preeclampsia. An imbalance in the ratio of thromboxane A2 to prostacyclin in preeclampsia has been proposed as a major pathological mechanism in preeclampsia (Walsh 1988, Fitzgerald 1987, Friedman 1988). Other experimental studies (unreported) in pregnant rats and guinea pigs indicate that nitric oxide deficiency is the primary event in preeclampsia. Inhibition of nitric oxide synthesis during pregnancy with L-NAME caused the classical symptoms hypertension, proteinuria and fetal growth retardation.

Prostacyclin is available as a stable freeze-dried preparation, viz., epoprostenol, for intravenous administration to man. A major limitation of epoprostenol is the need to administer it parenterally, the steep dose-response relationship for both platelet inhibition and the appearance of side effects, and its short duration of action (Moran and Fitzgerald 1994; Vane 1993). The marked fall in systemic blood pressure, especially associated with the use of epoprostenol, or intravenous iloprost, is why the use of prostacyclin and its analogs has not gained widespread use in the management of cardiovascular disorders (Vane 1993).

There have been attempts to treat preeclampsia with prostacyclin. Prostacyclin consistently relaxes placental blood vessels when tested in vitro (Glance 1986, Howard 1986, Maigaard 1986). However, when tested in vivo, infusion of prostacyclin did not result in the increase in placental perfusion in sheep (Phernetton 1979, Rankin 1979, Landauer 1985) and humans (Husslein 1985). Moreover, studies in the sheep model have also demonstrated that prostacyclin infusion leads to a decrease of placental perfusion with resulting detrimental effects on the fetus.

When it became evident that there exists an imbalance of increased thromboxane and decreased prostacyclin production in preeclampsia, some investigators attempted to treat this disease by means of a constant i.v. infusion of prostacyclin. There are 3 reports on 7 women with severe preeclampsia who were treated with prostacyclin (4–8 ng/kg/min, 5 h to 11 days) after failure of conventional medication (Fidler 1980, Lewis 1981, Belch 1985). In all women, there was a rapid decrease in blood pressure during prostacyclin infusion. The clinical outcome of these studies was poor. All babies were delivered prematurely by cesarean section and only 4/7 babies survived. Fetal bradycardia was observed during treatment and two fetuses died during prostacyclin infusion. The prostacyclin treatment caused a steal phenomenon in these studies and actually decreased uteroplacental blood flow. This explanation is supported by a study of prostacyclin effects in 2 cases of severe early-onset fetal growth retardation. Intravenous prostacyclin was administered in an attempt to promote fetal growth and thus prolong pregnancy. This attempt was unsuccessful and resulted in intrauterine death in each case. In this report the infusion rate of 4 ng/kg/min. was limited by maternal side effects (Steel and Pearce 1988).

These observations indicate that treatment of already established preeclampsia with high-dose prostacyclin is an ineffective and risky strategy. On the other hand, there are no effective methods for the prevention of preeclampsia. Aspirin, when given to inhibit prostaglandin synthesis in relatively low doses, is thought to predominantly suppress the platelet thromboxane A2 production with little inhibition of the vascular prostacyclin production (Massoti 1979). Therefore, low-dose aspirin was proposed for the prevention of preeclampsia. The results of the recently published multicentric study are disappointing, and low-dose aspirin is currently not recommended for the prevention of preeclampsia (CLASP Collaborative Group, 1994). Thus there is need for an effective and safe method of prevention and treatment of preeclampsia.

The unexpected results of the studies described below indicate that the response of blood vessels to prostacyclins and subsequent blood pressure lowering effect is controlled by progesterone. Treatment of pregnant rats with the nitric oxide inhibitor (L-NAME) produces signs and symptoms of preeclampsia (e.g., hypertension, fetal retardation and proteinurea—the classical triad of preeclampsia). These symptoms are related to the decrease in vascular resistance and placental perfusion. In the rat model of preeclampsia (inhibition of nitric oxide synthesis with L-NAME), the blood pressure-lowering effects of cicaprost and iloprost are greater in late pregnancy when progesterone levels are elevated in pregnant rats. Post-partum, when progesterone blood concentrations decrease, there is a rapid increase in blood pressure in animals treated with L-NAME and cicaprost or iloprost. Injection of a progesterone receptor agonist R5020 (promegestone) restores the efficacy of iloprost/cicaprost to lower blood pressure. In addition progesterone partially lowers blood pressure in L-NAME-treated male rats and the antiprogestin RU 486 elevates blood pressure in this model. Thus, the condition of pregnancy and the progestin treatment highly increase the responsiveness of blood vessels to exogenous prostacyclin. The increased response of blood vessels results in the lowering of the effective dose of prostacyclin analogs and subsequently in the reduction of side effects. The treatment of preeclamptic rats with a combination of prostacyclin and a progestin is thus highly effective in lowering blood pressure and fetal mortality and in reversing fetal growth retardation.

A prostacyclin analog in combination with a progestational agent reverses the blood pressure increase induced by the inhibition of nitric oxide. Thus, prostacyclin in combination with progesterone can fully compensate the nitric oxide deficiency. These observations indicate that both the prostacyclin and nitric oxide systems are complementary (and exchangeable) with regard to blood pressure control.

Preeclampsia is a well known model of atherosclerosis as the decrease in placental is accompanied by increased fibrin deposition in placental vessels and increased thrombus formation. Therefore, this regimen is also effective in preventing and treatment of atherosclerotic disease in both female and male mammals.

It is well known that estrogen up-regulates the progesterone receptors in a variety of target organs. Therefore, concurrent estrogen administration with a progestin is preferred.

OBJECTS OF THE INVENTION

It is an object of the Invention to provide a method for the prevention and treatment of atherosclerotic vascular disease (cardiovascular disease) in both female and male mammals, with a combination of prostacyclin or a stable analog thereof, e.g., iloprost and cicaprost, with a progestogen and/or estrogen.

It is a further object to provide a method for hormone replacement therapy (HRT) in the peri- and post-menopausal female using an estrogenic agent in combination with prostacyclin or a stable analog thereof.

It is another object to provide a method for hormone replacement therapy (HRT) in the peri- and post-menopausal female using a combination of an estrogenic agent and a progestin agent with prostacyclin or a stable analog thereof.

It is another object to provide such a method in which a progestin and/or estrogen is used in combination with prostacyclin or a stable analog thereof for the prevention and treatment of preeclampsia in pregnant mammals.

It is another object to provide such a method in which an progestin and/or estrogen is used in combination with prostacyclin or a stable analog thereof, e.g., iloprost and cicaprost, for the treatment of hypertension, both in female and male mammals.

A further object is the provision of pharmaceutical compositions useful in practicing the methods of this invention.

Other objects will be apparent to those skilled in the art to which this invention pertains.

SUMMARY OF THE INVENTION

In a method aspect, this invention relates to a method of preventing and treating atherosclerotic vascular disease (cardiovascular disease) in both female and male mammals, including the treatment of preeclampsia in a pregnant female mammal and treating hypertension in both female and male mammals, which comprises administering to a subject manifesting the symptoms thereof (a) a prostacyclin or a prostacyclin analog, e.g., in an amount bioequivalent to 0.1–10 ng/kg/min of prostacyclin intravenously, and (b) one or both of a progestin and an estrogen, e.g., an amount of estrogen bioequivalent to approximately 2 mg per day of estradiol and an amount of progestin bioequivalent to 50–300 mg of injected progesterone, effective to ameliorate the symptoms.

In a product aspect, this invention relates to a pharmaceutical composition comprising at least one of the prostacyclin analog in combination with one or more of an estrogen and/or progestin with the amount of the estrogen being bioequivalent to about 2 mg of estradiol (e.g. "Progynova, R.", Schering, A. G.) with the amount of the progestin being bioequivalent to 50–300 mg of injected progesterone.

Other aspects will be apparent to those skilled in the art to which this invention pertains.

DETAILED DISCLOSURE

The compositions of this invention can be used to prevent and treat atherosclerotic vascular disease (cardiovascular disease) and treat hypertension in both female and male mammals, preferably human, and used for hormone replacement therapy in peri- and postmenopausal women. The methods of this invention can prevent and treat preeclampsia in pregnant mammals, e.g., a human who is manifesting the symptoms thereof or who is a high risk candidate for doing so, e g., as determined by the progress of a present or previous pregnancy.

Since the female sex steroids (progesterone and estrogens) act synergistically with prostacyclin and its analogs, a combination of a prostacyclin analogs with a progestin, an estrogen or both an estrogen and a progestin, is employed. A synergistic effect is achieved when a progestational and/or estrogenic agent is administered concurrently with the prostacyclin or prostacyclin analog.

Thus, the method aspect of this invention and the pharmaceutical composition aspect of this invention employs prostacyclin or a prostacyclin analog and one or more of an estrogen (e.g, estradiol valerate, conjugated equine estrogens, 17β-estradiol, estriol or ethinyl estradiol such as "Pyrgynova R", Schering, A. G.) and a progestin (e.g., progesterone, dydrogesterone, medroxyprogesterone, norethisterone, levonogestrel, norgestrel or gestoden).

Examples of combinations of prostacyclin analogs which are administered concurrently with a progestin and/or an estrogen are: prostacyclin (epoprostenol), iloprost, cicaprost. The following are typical oral dosage ranges active agents of the estrogen and progestin with a prostacyclin analog:

Prostacyclin: Iloprost, 10–1000 μg/patient; twice-a-day orally; Cicaprost, 1–100 pg/patient; twice-a-day orally.

Estrogens: a daily dose bioequivalent to about 1 to 2 mg per day, eg., "Premarin R" (Wyeth-Ayerst), 0.625 mg/day; estradiol valerate, 50 U9/day transdermally, vaginal estradiol creams, 1.25 mg/day and vaginal estradiol rings, 0.2 mg/day.

Progestins: A daily dose bioequivalent to 50–300 mg of progesterone/day, e.g., an injectable suspension of medroxyprogesterone acetate, to provide a weekly dose of thereof of 100–1000 mg in tablets or dragees providing an oral dose thereof of 5–10 mg/day, an injectable solution of hydroxyprogesterone caproate which provides a weekly dose of 250–500 mg; tablets, capsules or dragees of northindrone acetate which provide a daily dose of 5–20 mg.

Examples of estrogens and progestins are listed below. (Oral "natural" estrogens used in hormone replacement therapy currently available in the UK.)

| Product | Composition | Dose (mg per day) |
| --- | --- | --- |
| Climaval (Sandoz) | Oestradiol valerate | 1 or 2 |
| Progynova (Schering) | Oestradiol valerate | 1 or 2 |
| Harmogen (Abbott) | Piperazine oestrone sulfate | 1.5 or 2.5 |
| Hormonin (Shire) | Oestradiol +Oestrone +Oestriol | 0.6 |
| "Premarin" (Wyeth-Ayerst) | Conjugated equine estrogens | 0.625 or 1.25 or 2.5 |

Commercially available combination calendar packs or hormone replacement therapy include "Estrapak", "Prempak-C", "Trisequens", "Trisequens forte" and "Cycloprogynova". The following are illustrative compositions of such products: Oestradiol 50 mg per day (28 days, 8 patches); Conjugated equine estrogens 0.625 mg per day (28 days); Oestradiol valerate 2 mg per day (11 days); Oestradiol valerate 2 mg per day; Norgestrel 0.5 mg per day (12 days); Norgestrel 0.15 mg per day (12 days); Conjugated equine estrogens 1.25 mg per day (28 days); Norethisterone acetate 1 mg per day (10 days); Oestradiol 1 mg per day+oestriol 0.5 mg per day (6 days); Norethisterone acetate 1 mg per day (10 days); Oestradiol 1 mg per day+oestriol 0.5 mg per day (6 days); Oestradiol valerate 1 mg per day (21 days); Levonorgestrel 0.25 mg per day (10 days); Oestradiol valerate 2 mg per day (21 days); Levonorgestrel 0,5 mg per day (10 days).

Daily doses of progestogen to be taken for 12 days per month by patients receiving oral or transdermal estrogens: Norethisterone, 0.7–2.5 mg per day; medroxyprogesterone acetate, 10 mg per day; norgestrel, 150 mg per day; and dydrogesterone, 10–20 mg per day.

The pharmacologically active agents employed in this invention can be administered in admixture with conventional excipients, i.e., pharmaceutically acceptable liquid, semi-liquid or solid organic or inorganic carriers suitable, e.g., for parental or enteral application and which do not deleteriously react with the active compound in admixture therewith. Suitable pharmaceutically acceptable carriers include but are not limited to water, salt solutions, alcohols, vegetable oils, polyethylene glycols, gelatin, lactose, amylose, magnesium stearate, talc, silicic acid, vicious paraffin, perfume oil, fatty acid monoglycerides and diglycerides, pentaerythritol fatty acid esters, hydroxy methylcellulose, polyvinyl pyrrolidone, etc.

The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parental application, particularly suitable are solutions, preferably oily or aqueous solutions, as well as suspensions, emulsions, or implants, including suppositories and transdermal patches. Ampoules are convenient unit dosages.

In a preferred aspect, the composition of this invention is adapted for ingestion.

For enteral application, particularly suitable are unit dosage forms, e.g., tablets, dragees or capsules having talc and/or a carbohydrate carrier or binder or the like, the carrier preferably being lactose and/or corn starch and/or potato starch; particulate solids, e.g., granules; and liquids and semi-liquids, e.g., syrups and elixirs or the like, wherein a sweetened vehicle is employed. Sustained release compositions can be formulated including those wherein the active compound is protected with differentially degradable coatings, e.g., by microencapsulation, multiple coatings, etc.

Suitable for oral administration are, inter alia, tablets, dragees, capsules, pills, granules, suspensions and solutions. Each unit dose, e.g., each tablespoon of liquid or each tablet, or dragee contains, for example, 5–5000 mg of each active agent.

Solutions for parenteral administration contain, for example, 0.01–1% of each active agent in an aqueous or alcoholic solution.

The prostacyclin analog can be administered as an admixture with an estrogen and/or progestin and any other optional active agent or as a separate unit dosage form, either simultaneously therewith or at different times during the day from each other.

The combination of active agents is preferably administered at least once daily (unless administered in a dosage form which delivers the active agents continuously) and more preferably several times daily, e.g., in 2 to 6 divided doses.

In humans, both a prostacyclin analogue and progesterone (or bioequivalent of another progestin) should be given in a ratio which produces blood plasma levels of about 30–100 $\mu$molar progesterone and 500 to 1000 nmolar of estradiol.

BRIEF DESCRIPTION OF DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DISCUSSION OF THE DRAWINGS

Figure 1:
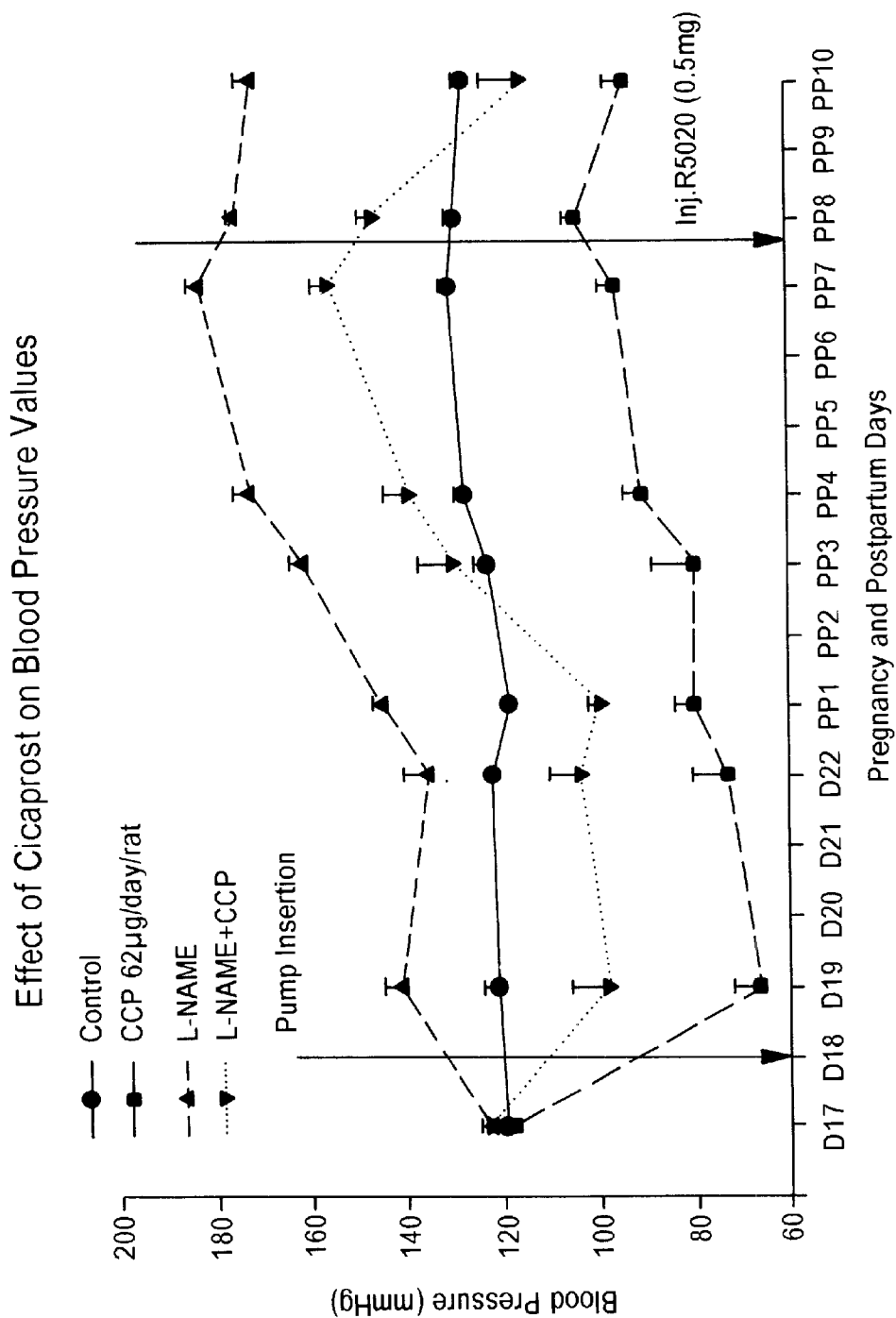
FIG. 1 demonstrates that the progesterone agonist R 5020 lowers blood pressure in the postpartum period in preeclamptic rats treated with cicaprost (CCP). Preeclampsia was induced with an nitric oxide inhibitor L-NAME (25 mg/animal/day, s.c. infusion). The blood pressure changes with cicaprost plus L-NAME during pregnancy parallel the endogenous levels if progesterone (a fall in blood pressure when progesterone levels are high-prepartum and an increase when progesterone levels are low postpartum.

The results shown in the drawings confirm that progesterone controls the action of a prostacyclin by increasing vascular responsiveness to this agent.

Figure 2:
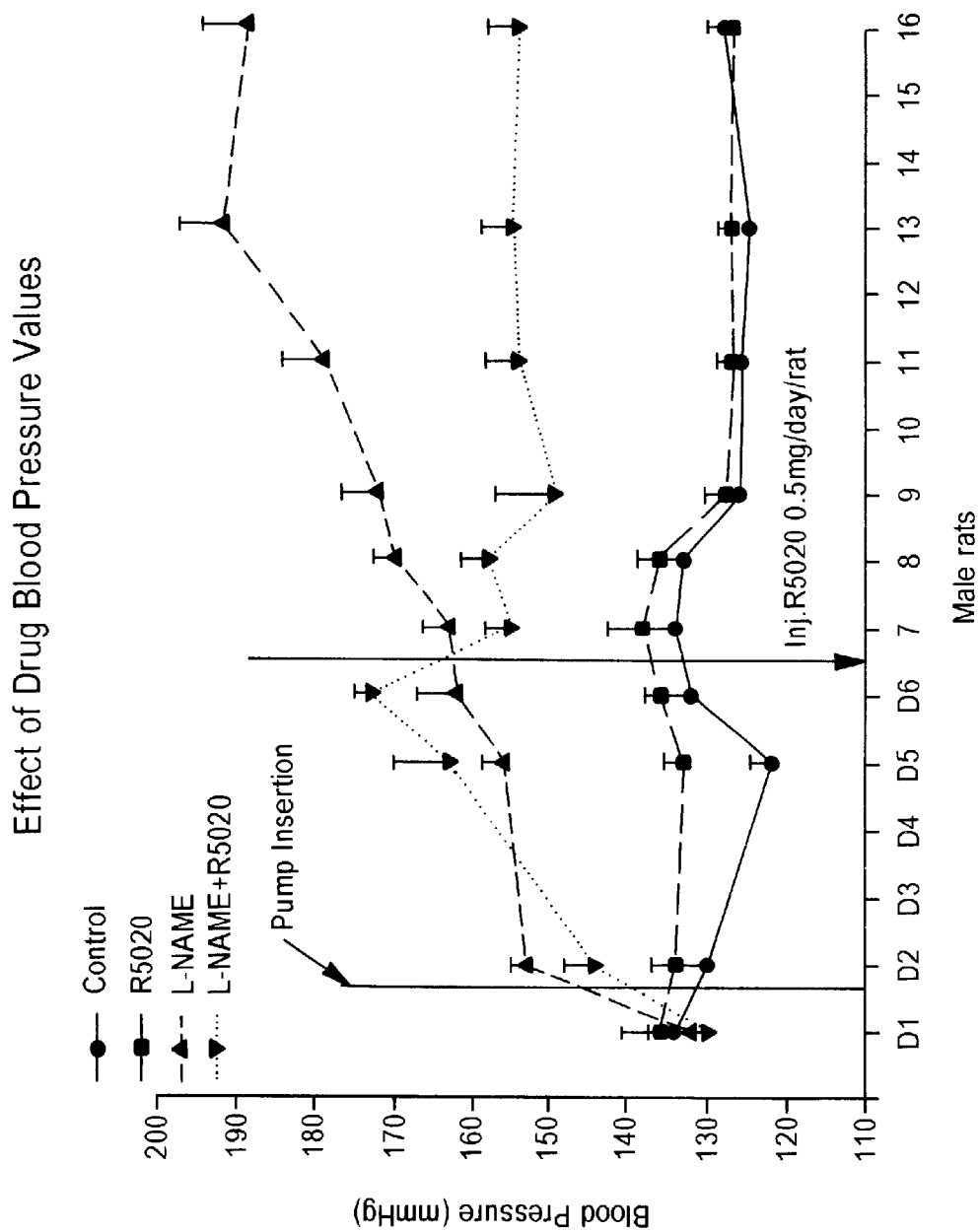
FIG. 2 shows that R 5020 (0.5 mg/animal/day s.c.) reduces the L-NAME-induced hypertension in male rats.
Figure 3:
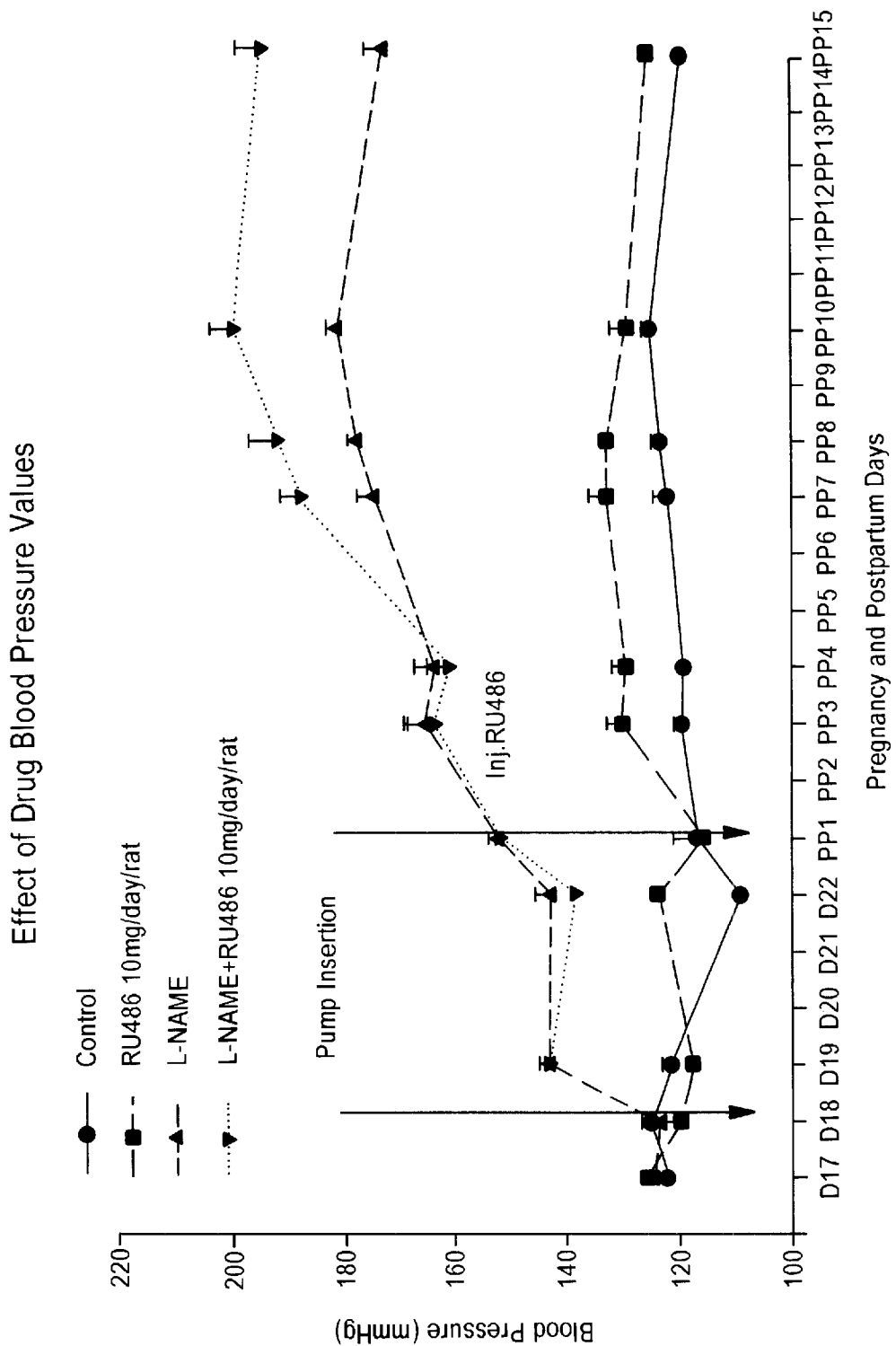
FIG. 3 shows that RU 486 elevates blood pressure post partum in animals treated with L-NAME and slightly increases blood pressure in controls.
Figure 4:
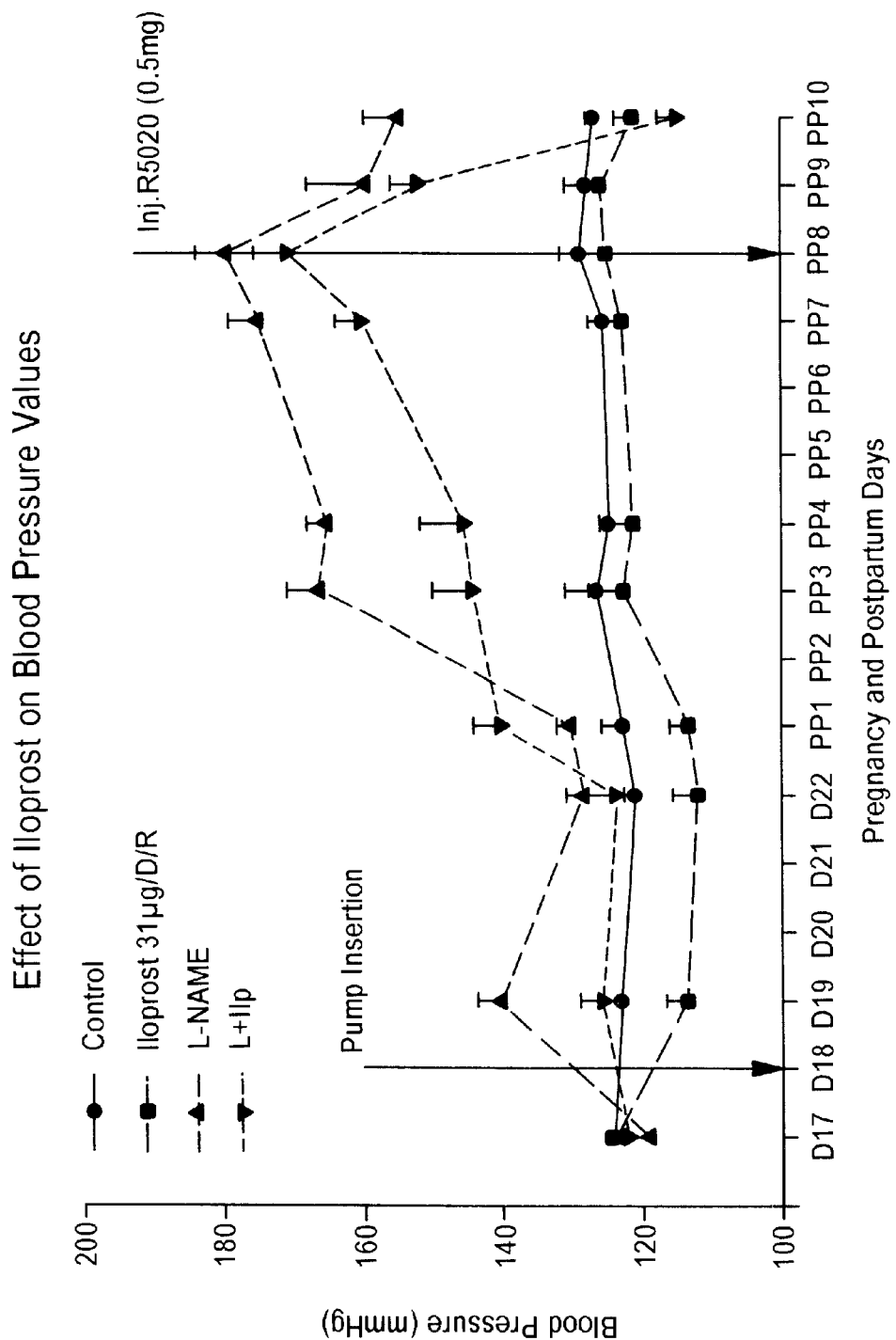
FIG. 4 shows that iloprost fully reverses the L-NAME-induced hypertension during pregnancy when progesterone levels are high, but there is an increase in blood pressure post-partum. R 5020 (5 mg/animal/day) dramatically decrease the post-partum increase in blood pressure.
Figure 5A:
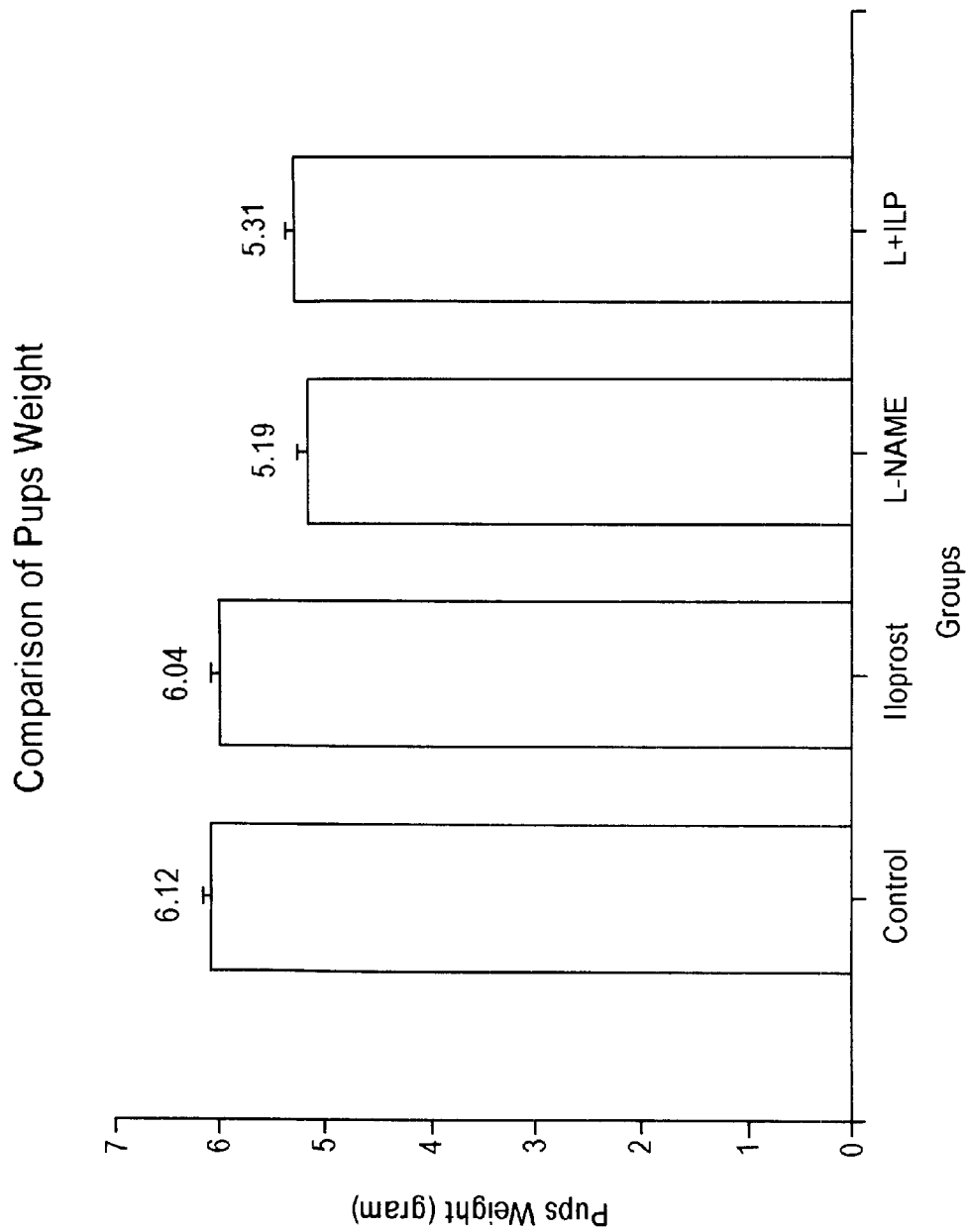
FIG. 5 is a bar chart which shows that iloprost partially reverses the L-NAME-induced fetal growth retardation (upper panel) and reduces the L-NAME-induced fetal mortality (lower panel).
Figure 5B:
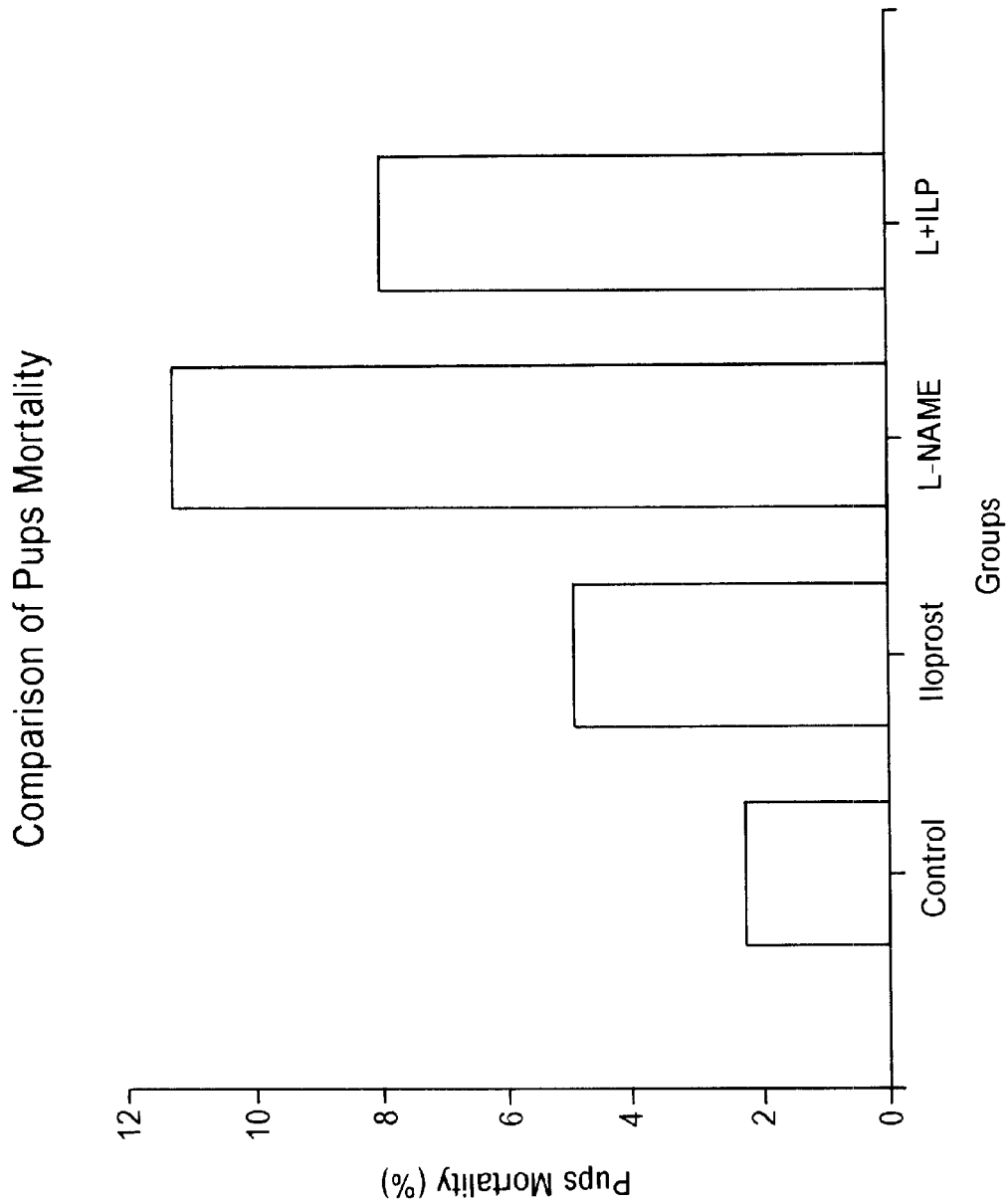

In the experiments whose results are shown by the graph of FIG. 1, a specific progesterone agonist (R 5020) restores the postpartum decrease in the efficacy of cicaprost to lower blood pressure. This study also shows that pregnancy (high progesterone and estrogen levels) itself has a beneficial effect on hypertension induced by L-NAME. FIG. 2 provides further evidence that progesterone can induce mechanisms which compensate the L-NAME-produced hypertension. This study was performed in male rats, showing pregnancy is not essential for this effect. FIG. 3 demonstrates that the effect of R 5020 is mediated by the progesterone receptor, since the antiprogestin RU 486 has an opposite effect (further increase in blood pressure induced with L-NAME). FIG. 4 shows that during pregnancy (high progesterone and estrogen levels) iloprost has a similar blood pressure lowering effect as cicaprost and that this effect is highly attenuated post partum when progesterone levels fall. FIGS. 5a and 5b demonstrate that iloprost increases placental perfusion, since the fetal weight increased and fetal mortality decreased in animals treated with iloprost plus L-NAME in comparison with the L-NAME-treated group.

It can be concluded from these studies that the effects of prostacyclin of reducing blood pressure and increasing fetal perfusion are progesterone dependent. Further, since estrogen is required for progesterone actions to induce progesterone receptors, it can be inferred that estrogen is important for these effects. The method of treatment employed in this invention can thus be employed for the treatment of preeclampsia, atherosclerotic vascular disease, hypertension (in both females and males), and as an adjuvant in hormone replacement therapy.

References

Abdul-Karim, R., Assali, N. S., (1961) Pressor response to angiotensin in pregnant and nonpregnant women, *Am J Obstet Gynecol* 82:264

Adams, M. R., Wagner, J. D., Clarkson, T. B. (1992) Effects of estrogens and progestins on atherosclerosis in primates. In Ramwell, P., Rubanyj, G., Schillinger, E. (editors) *Sex steroids and the cardiovascularsystem*. Schering Foundation Workshop 5. Springer Verlag, p. 161–175

Belch, J. J. F., Thorburn, J., Greer, I. A., et al. (1985) Intravenous prostacyclin in the management of pregnancies complicated by severe hypertension. *Clin Exp Hyper Preg* B4:75

Bonnar, J., McNicol, G. P., Douglas, A. S. (1971) Coagulation and fibrinolytic systems in pre-eclampsia and eclampsia. *Br Med J* 2:12

Braun, M., et al. (1992), Antiatherosclerotic properties of oral cicaprost in hypercholesterolemic rabbits, In Sinzinger, H. F., Schror, K. (eds) *Prostaglandins in the Cardiovascular System*. Birkkauser Verlag, Basel, Boston, Berlin, pp. 282–288

Burton, G. A., et al. (1992). Iloprost preserves endothelial function against cyclosporin A and sensitizes towards endothelium-dependent and independent vasodilatation, In Sinzinger, H. F., Schror, K. (eds) *Prostaglandins in the Cardiovascular System*. Birkkauser Verlag, Basel, Boston, Berlin, pp. 340–345

CLASP Collaborative Group: CLASP: a randomized trial of low-dose aspirin for the prevention and treatment of preeclampsia among 9364 pregnant women. *Lancet* 343 (1994): 619–629

DeWolf, F., Robertson, W. B., Brosens, I. (1975) The ultrastructure of acute atherosis in hypertensive pregnancy. *Am J Obstet Gynecol* 123:164

Fidler, J., Bennett, M. J., De Swiet, M., et al., (1980) Treatment of pregnancy hypertension with prostacyclin. *Lancet* 2:31

Fitzgerald, D. J., Entman, S. S., Mulloy, K., et al. 1987(a) Decreased prostacyclin biosynthesis preceding the clinical manifestations of pregnancy-induced hypertension.

Fitzgerald, D. J., Mayo, G., Catella, F., Entmann, S. S., FitzGerald, G. A., 1987(b) Increased tromboxane biosynthesis in normal pregnancy as mainly derived from platelets. *Am J Obstet Gynecol* 157:325

Fitzgerald, D. J., Rocki, W., Murray, R., Mayo, G., FitzGerald, G. A. (1990) Thromboxane A2 synthesis in pregnancy-induced hypertension. *Lancet* 335:751

Friedman, E. A. (1988) Preeclampsia: a review of the role of prostaglandins. *Obstet Gynecol* 71,1: 122

Frusca, T., Morassi, L., Pecorelli, S., Grigolato, P., Gastaldi, A. (1989) Histological features of uteroplacental vessels in normal and hypertensive patients in relation to birth weight. *Brit J Obstet Gynaecol* 96,7:835

Furchgott R F, Zawadzki J V (1980) The obligatory role of endothelial cells in the relaxation of arterial smooth muscle by acetylcholine. *Nature* 288:373–76

Gangar K, F, Reid B A, Hillard T C, Whitehead M I (1993) Oestrogens and atherosclerotic vascular disease—local vascular factors. *Balliere s Clinical Endocrinology and Metabolism* 7: 47–59

Gant N F, Daley G L, Chand S, Whaley P J, MacDonald P C (1973) A study of angiotensin 11 pressor response throughout primigravid pregnancy. *J Clin Invest* 52:2682

Gant N F, Chand S, Whalley P J et al (1984): The nature of pressor responsiveness to angiotensin 11 in human pregnancy. *Obstet Gynecol* 43:854

Giles C, Inglis T C M (1981) Thrombocytopen-ia and macrothrombocytopenia in gestational hypertension, *Br J Obstet Gynecol* 82:35

Glance D E, Elder M G, Myatt L (1986) The actions of prostaglandins and their interactions with angiotensin 11 in the isolated perfused human cotyledon. *Br J Obstet Gynecol* 93:488

Greiss F C, Anderson S G (1970) Effect of ovarian hormones on the uterine vascular bed. *Am J Obstet Gynecol* 107:829–36

Green A, Bain C, (1993) Epidemiological overview of estrogen replacement and Goodman R P, Killam A P, Brash A R, Branch R A (1982) Prostacyclin production during pregnancy: comparison of production during normal pregnancy and pregnancy complicated by hypertension. *Am J Obstet Gynecol* 142: 817

Hohfeld T, Weber A, Schror K (1992) Oral cicaprost reduces platelet and neutrophil activation in experimental hypercholesterolemia. In Sinzinger H F, Schror K (eds) *Prostaglandins in the Cardiovascular System*. Birkkauser Verlag, Basel, Boston, Berlin, pp. 289–296

Howard R B, Hosakawa T, Maquire M H (1986) Pressor and depressor actions of prostanoids in the intact human fetoplacental vascular bed. *Prostagl Leuk Med* 21:323

Husslein P, Gitsch E, Pateisky N, Philipp K, Leodolter S, Sizinger H (1985) Prostacyclin does not influence placental blood pool in vivo. *Gynecol Obstet Invest* 19:78

Landauer M, Phernetton T M, Parisi V M 1985 Ovine placental vascular response to the local application of prostacyclin. *Am J Obstet Gynecol* 151:460

Lewis P J, Shepard G L, RitterJ et al (1981) Prostacyclin in preeclampsia. *Lancet* 1:559

Lin A L, Gonzales R Jr, Carey K D, Shain S A (1986) Estradiol 17-beta affects estrogen receptor distribution and elevates progesterone receptor content in baboon aorta. *Atherosclerosis* 6:495–504

Magness R R (1991) Endothelium-derived vasoactive substances and uterine blood vessels. *Semin Perinatol* 15:68–78

Massotti G, Galanti G. Poggesi L, Abbate R, Neri-Serneri G G (1979) Differential inhibition of prostacyclin production and platelet aggregation by aspirin. *Lancet* 2:1213

Moncada S, Palmer R M G, Higgs E A (1991) Nitric oxide: physiology, pathophysiology and pharmacology. *Pharmacological Reviews* 43:109–142

Moran N, Fitzgerald G A (1994) Mechanism of action of antiplatelet drigs. In: Colman R W, Hirsch J, Marder V J, Salzman E W: Hemostasis and Thrombosis. *Basic Principles and Clinical Practice*, 3rd ed. Lippincott, Philadelphia, 1994: pp 1623–1637

Perkins R P (1979) Thrombocytopenia in obstetric syndromes: a review *Obstet Gynecol Surv* 34:101

Phernetton T M, Rankin J H G (1979) Effect of prostaglandin blood flow on ovine maternal and fetal adrenal blood flows. *Proc Soc Exp Biol Med* 162:324

Rankin J H G, Phemetton T M, Anderson D F et al (1979) Effect of prostaglandin 12 on ovine placental vasculature. *J Dev Physiol* 1:151

Remuai G, Marchesi D, Mecca G at al (1980) Reduction of fetal vascular prostacyclin activity in pre-eclampsia. *Lancet* 2:310

Roberts J M, (1989) Pregnancy related hypertension. In Creasy R K, Resnik R (eds) *Maternal fetal medicine: principles and practice*. Philadelpha:W B Saunders Roberts J M, Taylor R N, Musci T J, Rodgers G M, Hubel C A, McLaughlin M K (1989) Preeclampsia: an endothelial cell disorder. *Am J Obstet Gynecol* 161,5:1200

Robertson W B, Brosens I, Dixon H G (1967) The pathological response of the vessels of the placental bed to hypertensive pregnancy. *J Path Bact* 93:581

Robertson W B, Khong T Y, Brosens I, Wolf F D (1986) The placental bed biopsy: review from three European centers. *Am J Obstet Gynecol* 159:401

Skuballa W, Raduchel B, Vorbruggen (1985) Chemistry of a stable prostacyclin analogues: Synthesis of iloprost. In Gryglewski R J, Stock G (eds) *Prostacyclin and its stable analogue iloprost*. Springer-Verlag Berlin, :17–25

Skuballa W E, Schillinger E, Sturzebecher C S, Vorbruggen H (1986) Synthesis of a new chemically and metabolically stable prostacyclin analogue with high and longlasting oral activity. *J Med Chem* 29: 313

Shanklin D R, Sibai B M (1989) Ultrastructural aspects of preeclampsia. I. Placental bed and uterine boundary vessels. *Am J Obstet Gynecol*: 161,3 735

Stampfer M J, Willet W C, Colditz G A, Rosner B, Speizer F E, Hennekens C H (1985) A prospective study of postmenopausal therapy and coronary-heart disease. *N Engl J Med* 313:1044–9

Stamfer M J (1992) A review of the epidemiology of postmenopausal estrogens and the risk of coronary heart disease.In Ramwell P, Rubanyi G, Schillinger E. (editors) *Sex steroids and the cardiovascularsystem*. Schering Foundation Workshop 5. SpringerVerlag, p. 177–197

Steel S A, Pearce J M (1988) Specific therapy in severe fetal growth retardation: failure of prostacyclin.*J Roy Soc Med* 81: 214–216

Topozada M, Khowessah M, Shala S, Shalaby T (1986/1987) Effect of prostacyclin infusion in severe pre-eclampsia. *Clin Exper Hyper Preg* B5(3):331

Van Buren G A, Yang D, Clark K E (1992) Estrogen-induced uterine vasodilatation is antagonized by L-nitroarginine methy ester, an inhibitor of nitric oxide synthesis. *Am J Obstet Gynecol* 167:828–33

Walsh S W (1985) Preeclampsia: an imbalance in placental prostacyclin and thromboxane production. *Am J Obstet Gynecol* 152:335

Walsh S W, Parisi V M 1986 The role of arachidinic acid metabolism in preeclampsia. *Sem Perinatol* 10,4:334

Willis A L, Smith D L (1989) Therapeutic impact of eicanoids in atherosclerotic disease.*Eicosanoids* 2: 69–99

Woditsch I, et al., (1992), In Sinzinger HF, Schror K (eds) *Prostaglandins in the Cardiovascular System*. Birkkauser Verlag, Basel, Boston, Berlin, pp. 297–304

Vane I R: The Croonian Lecture, 1993. The endothelium: maestro of the blood circulation. Phil Trans R Soc London (1994) 225–246

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever. The entire disclosure of all applications, patents and publications, cited above and below are hereby incorporated by reference.

EXAMPLES

Example 1

Prevention of Atherosclerotic Vascular Disease With Iloprost and an Estrogen/Progestin Combination To a non-pregnant human female (ca 45 years; 50–80 kg) displaying the signs of menopause or postmenopausal symptoms administer an estrogen (e.g. estradiol valerate 1–2 mg daily) a progestin (e.g. norgestrel 150 μg per day) and 50 μg iloprost twice-a-day orally.

Example 2

Prevention of Atherosclerotic Disease With Cicaprost and Estrogen Plus Progestin Hormone Replacement Therapy To a human female comparable to and displaying the same symptoms as Example 1, administer daily one or both of the following, an estrogen (e.g. estradiol valerate) 1–2 mg daily, and a progestin (e.g., norgestrel, at 150 mg per day). The estrogen is administered with a prostacyclin, e.g., iloprost or cicaprost either continuously or sequentially with a progestin taken for only 6–12 days per month.

Example 3

Prevention of Atherosclerotic Vascular Disease With Iloprost and Estrogen

To a human female similar to and displaying the same symptoms as Example 1, administer daily in combination with an estrogen (e.g. estradiol valerate, 1–2 mg daily) 50 μg iloprost twice-a-day orally.

Example 4

Treatment of Atherosclerotic Vascular Disease With Iloprost and Progesterone

To human male (ca 45 years; 50–80 kg) displaying the signs of cardiovascular disease administer a progestin (e.g. norgeststrel 150 μg per day) and 50 μg iloprost twice-a-day orally.

Example 5

Treatment of Hypertension Iloprost and Progesterone

To a human female or male and displaying hypertension, administer 50 μg iloprost twice-a-day orally with a progestin (e.g. norgestrel) 150 mg per day.

Example 6

Prevention of Preeclampsia With Iloprost and Progesterone

To a pregnant human female displaying the symptoms of preeclampsia, administer 50 μg iloprost twice-a-day orally with progesterone (e.g. 200 mg micronized progesterone per os.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treatment selected from the group consisting of (a) preventing or treating atherosclerotic vascular disease in a mammal; b) hormone replacement therapy in a peri- or post-menopausal female mammal; and c) treating hypertension in a mammal, which comprises administering to the afflicted mammal an amount of prostacyclin or prostacyclin analog in combination with one or more of an estrogen and a progestin, in amounts effective to ameliorate or prevent the appearance of the symptoms thereof, wherein said amounts are synergistically effective and the amounts of prostacyclin, prostacyclin analog, estrogen or progesterone are individually ineffective or marginally effective.

2. The method of claim 1, wherein the mammal is a human female suffering from menopausal or postmenopausal symptoms of climacterium.

3. The method of claim 1, wherein the mammal is a human female who is a candidate for hormone replacement therapy.

4. The method of claim 1, wherein the mammal is a human male suffering from cardiovascular disease.

5. The method of claim 1, wherein the mammal is a human suffering from hypertension.

6. The method of claim 1, wherein the mammal is a pregnant human female suffering from preeclampsia.

7. The method of claim 1, wherein the mammal is a human and the prostacyclin or prostacyclin analog administered thereto is iloprost or cicaprost.

8. The method of claim 7, wherein a prostacyclin analog is administered orally.

9. The method of claim 1, wherein the mammal is a human and the prostacyclin or prostacyclin analog is administered thereto in combination with a progestin.

10. The method of claim 9, wherein the progestin is progesterone, dydrogesterone, medroxyprogesterone, norethisterone, levonorgestrel or norgestrel.

11. The method of claim 1, wherein the mammal is a human female and the prostacyclin or prostacyclin analog is administered thereto in combination with an estrogen.

12. The method of claim 11, wherein the estrogen is estradiol valerate, conjugated equine estrogens, 17β-estradiol, estrone, estriol or ethinyl estradiol.

13. The method of claim 1, wherein the mammal is a human female and the prostacyclin or prostacyclin analogue is administered thereto in combination with both an estrogen and a progestin.

14. The method of claim 1, wherein the mammal is a human female and the estrogen or progestin are administered thereto continuously.

15. The method of claim 1, wherein the mammal is a human female and an estrogen and a progestin are administered thereto sequentially.

16. A pharmaceutical composition comprising an admixture of (a) prostacyclin or prostacyclin analog and at least one of (c) an estrogen and (d) a progestin, wherein the amounts of (a) and (c) and/or (d) are synergistically effective and are individually ineffective or marginally effective.

17. The composition according to claim 16, comprising an amount of an estrogen equivalent to 1–2 mg of estradiol and/or an amount of a progestin bioequivalent to 50–300 mg of injected progesterone.

18. The composition according to claim 16, wherein (a) is iloprost or cicaprost.

19. The composition according to claim 16, comprising an estrogen.

20. The composition according to claim 20, wherein the estrogen (b) is estradiol valerate.

21. The composition according to claim 16, comprising a progestin.

22. The composition according to claim 21, wherein the progestin (d) is norgestrel.

23. The composition according to claim 16, comprising both a progestin and an estrogen.

* * * * *